(12) United States Patent
Lin et al.

(10) Patent No.: US 6,608,040 B1
(45) Date of Patent: Aug. 19, 2003

(54) CHEMICAL MODIFICATION OF BIOMEDICAL MATERIALS WITH GENIPIN

(75) Inventors: Ching-Kuan Lin, Taichung (TW); Thomas Chau-Jen Lee, deceased, late of Walnut Creek, CA (US), by Huey Li Lee, legal representative; Hsing-Wen Sung, Hsinchu (TW)

(73) Assignee: Challenge Bioproducts Co., Ltd., Taichung (TW)

( * ) Notice: Subject to any disclaimer, the term of this patent is extended or adjusted under 35 U.S.C. 154(b) by 0 days.

(21) Appl. No.: 09/297,808

(22) Filed: Sep. 27, 2001

Related U.S. Application Data

(60) Provisional application No. 60/030,701, filed on Nov. 5, 1996.

(51) Int. Cl.⁷ ...................... A01N 43/04; A61K 31/715
(52) U.S. Cl. ............................ 514/54; 424/422; 514/55
(58) Field of Search .................... 514/54–60, 6

(56) References Cited

U.S. PATENT DOCUMENTS

| 5,037,664 | A | * | 8/1991 | Kyogoku et al. ............ 426/573 |
| 5,270,446 | A | * | 12/1993 | Kyogoku et al. ............ 530/300 |
| 5,521,154 | A | * | 5/1996 | Garlick et al. ................. 514/6 |
| 6,077,988 | A | * | 6/2000 | Kuberasampath et al. .... 623/16 |

FOREIGN PATENT DOCUMENTS

| EP | 0366998 | * | 5/1990 | ............ A23L/1/48 |

OTHER PUBLICATIONS

Fujikawa, S.; Nakamura, S.; Koga, K. Agric. Biol. Chem. 52(3), 869–70, 1988.*
Bëchi, G. et al., J. Am. Chem. Soc. 89:2776–7 (1967).
Chang, T.M.S. et al., Biomater. Artif. Cells Immobilization Biotech, 20:159–179 (1992).
Kometani, T. et al., Bio Sci. Biotechnol. Biochem. 57:1185–7 (1993).
Oka, H. et al., ACS Symposium Series 593 (Modern Countercurrent Chromatography), 92–106 (1995).
Keipert, P.E. et al., Transfusion 29:768–773 (1989).

* cited by examiner

*Primary Examiner*—James O. Wilson
*Assistant Examiner*—Ganapathy Krishnan
(74) *Attorney, Agent, or Firm*—Bacon & Thomas

(57) ABSTRACT

Biocompatible cross-linked materials, suitable for use in implants, wound dressings, and blood substitutes, are described. The materials are prepared by cross-linking biological substances, such as collagen, chitosan, or hemoglobin, with genipin, a naturally occurring cross-linking agent. The cross-linking agent has much lower toxicity than conventionally used reagents, and the cross-linked products have good thermal and mechanical stability as well as biocompatibility.

17 Claims, 13 Drawing Sheets

  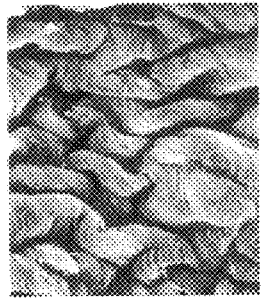 
Fig. 9A   Fig. 9B   Fig. 9C   Fig. 9D
  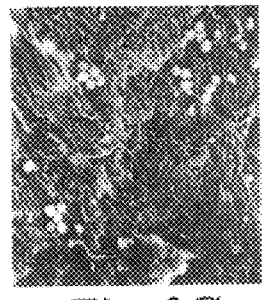 
Fig. 9E   Fig. 9F   Fig. 9G   Fig. 9H

CHEMICAL MODIFICATION OF BIOMEDICAL MATERIALS WITH GENIPIN

This application is a 371 of PCT/US97/20113, filed Nov. 4, 1997, which application claims benefit of the U.S. provisional application serial No. 60/030,701, filed Nov. 5, 1996.

FIELD OF THE INVENTION

The present invention relates to chemical modification of biomedical materials, such as collagen, chitosan, and hemoglobin, with a naturally occurring crosslinking reagent, genipin, and to biocompatible materials, useful in biological implants, adhesives, wound dressings, and blood substitutes, which are crosslinked or polymerized with genipin.

REFERENCES

Büchi, G. et al., *J. Am. Chem. Soc.* 89:2776–7 (1967).
Chanda, J. et al., *Artif Organs* 18(10):752–7 (1994).
Chandy, T. et al., *Proc. South. Biomed. Eng. Conf.*, 14th (1995), pub. by IEEE, New York, N.Y.
Chandy, T. et al., *Biomater., Artif. Cells, Artif. Organs* 18(1):1–24 (1990).
Chang, T. M. S. et al., *Biomater. Artif. Cells Immobilization Biotech.* 20:159–179 (1992).
Fujikawa, S. et al., *Biotechnol. Lett.* 9:697–702 (1987).
Hilbert, S. L. et al., *Med. Prog. Technol.* 14(3–4): 115–63 (1988).
Keipert, P. E. et al., *Transfusion* 29:768–773 (1989).
Khor, E., *Biomaterials* 18(2):95–105 (1997).
Kometani, T. et al., *Biosci. Biotechnol. Biochem.* 57:1185–7 (1993).
Li, S. T., in *Biotechnol. Polym.*, Gebelein, C. G., ed.., Technomic, Lancaster, Pa., 1993, pp. 66–81.
Oka, H. et al., ACS Symp. Series 593 (Modern Countercurrent Chromatography), 92–106 (1995).
Okada, S. et al., JP Kokai No. 5-276971 (1993).
Oliver, R. F., in *Biocompat. Tissue Analogs*, Vol. 1, Williams, D. F., ed.., CRC Press, Boca Raton, Fla., 1985, pp. 117–34.
Olsen, R. et al., *Proc. Int. Conf. Chitin Chitosan*, 4th (1988), Skjaak-Braek, G. et al., eds., Elsevier, London (1989).
Sabelman, E. E., in *Biocompat. Tissue Analogs*, Vol. 1, Williams, D. F., ed.., CRC Press, Boca Raton, Fla., 1985, pp. 27–66.
Stenzel, K. H. et al., *Polym. Sci. Techn.* 8:109–18 (1975).
Tanaka, M. et al., JP Kokai No. 2-300183 (1990).

BACKGROUND OF THE INVENTION

Crosslinking of biological molecules is often desired for optimum effectiveness in biomedical applications. For example, collagen, which constitutes the structural framework of biological tissues, has been extensively used for manufacturing bioprostheses and other implanted structures, such as vascular grafts, wherein it provides a good medium for cell infiltration and proliferation. Collagen sheets are also used as wound dressings, providing the advantages of high permeability to water vapor and rapid wound healing. Disadvantages of uncrosslinked collagen include low tensile strength and ready degradation by collagenase. The fixation, or crosslinking, of collagenous tissues increases mechanical strength, reduces cleavage by collagenase, and reduces antigenicity and immunogenicity.

Chitosan, a deacetylated derivative of chitin, contains free amino groups which may also be crosslinked, e.g. by glutaraldehyde (Jameela), and has been used or proposed for use in implanted drug-delivery devices, skin substitutes, wound dressings, and other biomaterials. It has shown the beneficial property of reducing calcification when coated on other implanted materials (Chanda).

Various crosslinking reagents have been used in the chemical modification of amine-containing biomedical materials. The most common are synthetic chemicals such as formaldehyde, glutaraldehyde, dialdehyde starch, glycoaldehyde, cyanamide, diimides, and diisocyanates. Of these, glutaraldehyde, which reacts rapidly with proteins, is the most commonly used.

Problems which have been encountered with crosslinked collagen include the tendency to calcify when implanted, leading to stiffness around an implant, eventual degradation and resorption into the surrounding tissue, and toxic reactions to crosslinking reagents. Glutaraldehyde is known to have allergenic properties, causing occupational dermatitis, and is cytotoxic at concentrations greater than 10–25 ppm and as low as 3 ppm in tissue culture.

Another useful application of crosslinked biological materials is in blood substitutes. Cell-free hemoglobin, a blood substitute, is useful for antigen-free blood transfusions, but is easily transformed from tetramer to dimer during circulation. High oxygen affinity and short half-life are additional limitations of this material. These difficulties may be overcome by chemical modification of hemoglobin with a crosslinking reagent (see e.g. Chang, Keipert). The increase of the half-life of hemoglobin in circulation and the reduction of its oxygen affinity can be achieved by both intermolecular and intramolecular crosslinking. Crosslinking with glutaraldehyde, however, has been found to induce dimer formation during hemoglobin polymerization.

It is therefore desirable to provide a crosslinking reagent suitable for use in biomedical applications which is of low toxicity, forms stable, biocompatible crosslinked products, and retains its stability upon implantation.

SUMMARY OF THE INVENTION

In one aspect, the invention provides a biocompatible implant or wound dressing. The implant or dressing is of a material which comprises a biocompatible crosslinked amine-containing biomolecule, selected from chitosan or a connective-tissue protein, where the biomolecule is crosslinked with genipin. Where the biomolecule is a connective-tissue protein, the protein is preferably collagen. Also provided is a biocompatible adhesive, which comprises a biocompatible crosslinked gelatin, derived from a collagenous source, where the gelatin is crosslinked with genipin.

In another aspect, the invention provides a method of manufacturing a biocompatible implant or wound dressing. The method includes the steps of fabricating a material which comprises an amine-containing biomolecule, selected from chitosan or a connective-tissue protein, into a structure suitable for the implant or dressing, and crosslinking the material with genipin. When the material comprises a connective-tissue protein, the protein is preferably collagen.

In other aspects, the invention provides a composition suitable for use in a blood substitute, which comprises hemoglobin crosslinked with genipin, and a method of preparing the composition, by treating hemoglobin with an amount of genipin effective to crosslink the hemoglobin. Preferably, the crosslinked hemoglobin has a mean degree of polymerization greater than 1 and less than about 9.

BRIEF DESCRIPTION OF THE FIGURES

FIGS. 9A–9H are computer-generated images derived from scanning electron micrographs (magnification×1,500) of (A) fresh tissue, (B) glutaraldehyde-fixed tissue, (C) epoxy-fixed tissue, and (D) genipin-fixed tissue, all before implantation, (E) the fresh tissue retrieved 1 week after implantation, and (F) glutaraldehyde-fixed tissue, (G) epoxy-fixed tissue, and (H) genipin-fixed tissue retrieved 12 weeks after implantation;

DETAILED DESCRIPTION OF THE INVENTION

I. Definitions

Figure 1A:
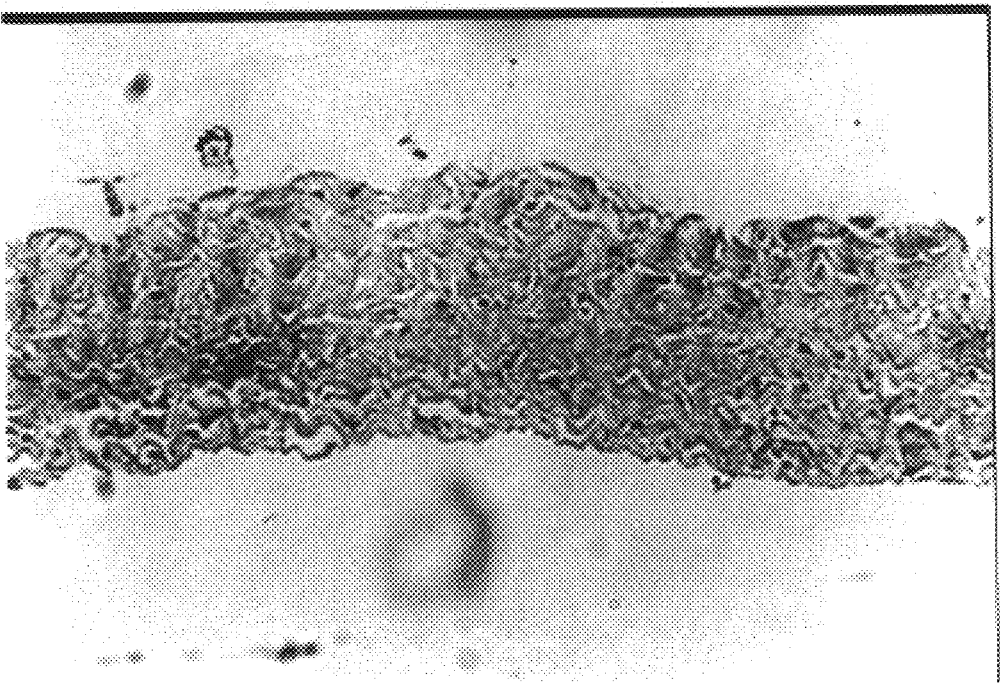
FIGS. 1A–H are computer-generated images derived from photomicrographs (X200) of uncrosslinked, or fresh tissues (1A–B), and tissues crosslinked with glutaraldehyde (GA) (1C–D), epoxy (EX-810) (1E–F), and genipin (1G–H), before and after collagenase degradation, respectively.

The terms below have the following meanings unless indicated otherwise.

"Genipin" refers to the naturally occurring compound shown as Structure I and to its stereoisomers and mixtures thereof.

A "collagenous material" or "collagenous source" refers to a material which largely comprises collagen, such as a sample of mammalian connective tissue, and is suitable for fabrication of a biological prosthesis, implant, graft, or wound dressing.

A "biological implant" refers to a biomedical device which is inserted into, or grafted onto, bodily tissue to remain for a period of time, such as an extended-release drug delivery device, vascular or skin graft, or prosthesis.

"Crosslinked hemoglobin" refers to hemoglobin which contains intramolecularly crosslinked hemoglobin, where crosslinks exist between individual chains in the tetrameric molecule, and/or intermolecularly crosslinked hemoglobin, or polyhemoglobin, where tetramneric molecules are linked together.

"Degree of polymerization" refers to the number of hemoglobin molecules linked together in a crosslinked hemoglobin. For example, the designation $Hb_2$ indicates two hemoglobin units joined by an intermolecular crosslink; they may be intramolecularly crosslinked as well.

II. Preparation and Properties of Genipin

Genipin, shown below as Structure I, is an iridoid glycoside present in fruits (Gardenia jasmindides Ellis). It may be obtained from the parent compound geniposide, structure II, which may be isolated from natural sources as described in, for example, Oka, Okada, or Kometani. Genipin, the aglycone of geniposide, may be prepared from the latter by oxidation followed by reduction and hydrolysis (Tanaka) or by enzymatic hydrolysis (Fujikawa). Alternatively, racemic genipin may be prepared synthetically, e.g. according to the method of Büchi.

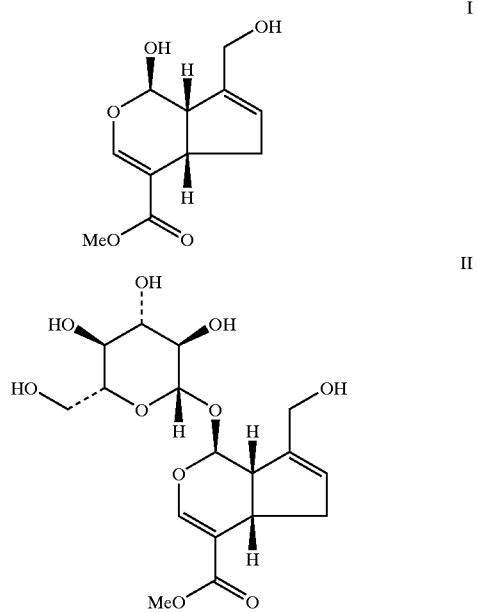

Although Structure I shows the natural configuration of genipin, any stereoisomer or mixture of stereoisomers of genipin may be used as a crosslinking reagent, in accordance with the present invention.

Genipin has a low acute toxicity, with $LD_{50}$ i.v. 382 mg/k in mice. It is therefore much less toxic than glutaraldehyde and many other commonly used synthetic crosslinking reagents.

As described below, genipin is shown to be an effective crosslinking agent for treatment of biological materials intended for in vivo biomedical applications, such as prostheses and other implants, wound dressings, and blood substitutes.

III. Crosslinking of Biological Structural Compounds with Genipin

The biological compounds which are crosslinked preferably include connective-tissue proteins such as collagen or elastin, or materials derived from such proteins, e.g. gelatin, which is produced by hydrolysis of collagen or collagenous tissues. Other amine-containing structural compounds, such as chitosan, may also be treated with genipin to produce biocompatible crosslinked materials.

The fabrication of such materials, particularly collagen, with or without crosslinking, into medical devices such as bioprostheses, skin and vascular grafts, and wound dressings is well established in the art. See, for example, discussion in "Prosthetic and Biomedical Devices", Kirk-Othmer Encyclopedia of Chemical Science & Technology, John Wiley & Sons, 1995, and additional references such as Hilbert, Khor, Li, Oliver, Sabelman, and Stenzel. For references to uses of chitosan in such applications, see, for example, Chandy (1990, 1995) Jameela, and Olsen.

Genipin-crosslinked collagenous tissues may also be used in homeostasis, by providing a biocompatible surface for blocking blood flow and supporting blood clotting. A biocompatible adhesive may be prepared by crosslinking a gelatin, derived from hydrolysis of collagen or hydrolytic treatment of a collagen-containing tissue, with an amount of genipin effective to give the desired adhesiveness and consistency.

For crosslinking collagenous tissues, an effective amount of genipin was found to be about 200 ml of a 5% solution for a 6×6 cm sheet of tissue, as described in Example 1. More or less reagent could be used depending on the desired crosslinking density. Similarly, for crosslinking of gelatin or chitosan, routine experimentation may be used to determine the amount of reagent appropriate for the desired characteristics in the final product.

As demonstrated below, genipin-fixed collagenous tissues are highly resistant to degradation by collagenase or pronase, and their biocompatibility is demonstrated in subcutaneous implant experiments. The following sections describe the properties, including enzyme resistance, retention of mechanical properties, and low toxicity, of collagen tissue samples crosslinked with genipin, compared to samples crosslinked with other commonly used reagents.

A. Stability to Degradative Enzymes

To determine the stability of collagenous fibers treated with various crosslinking reagents, tissue samples were treated with the reagents, subjected to degradation with collagenase or pronase, and examined, as described in Example 1 below.

Figure 1B:
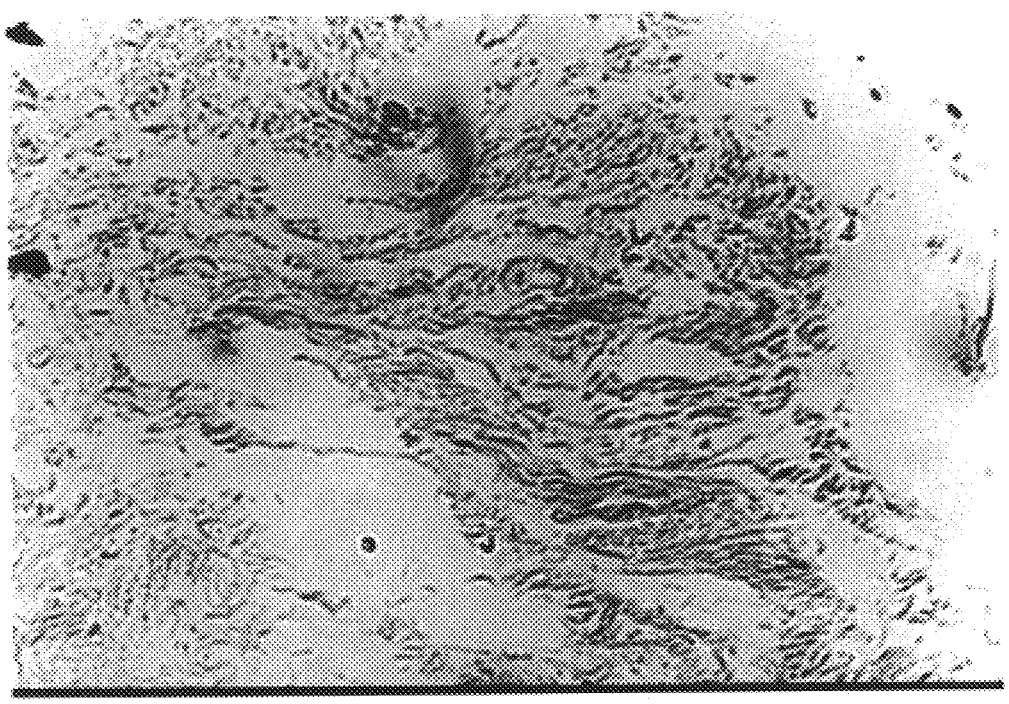
Figure 1C:
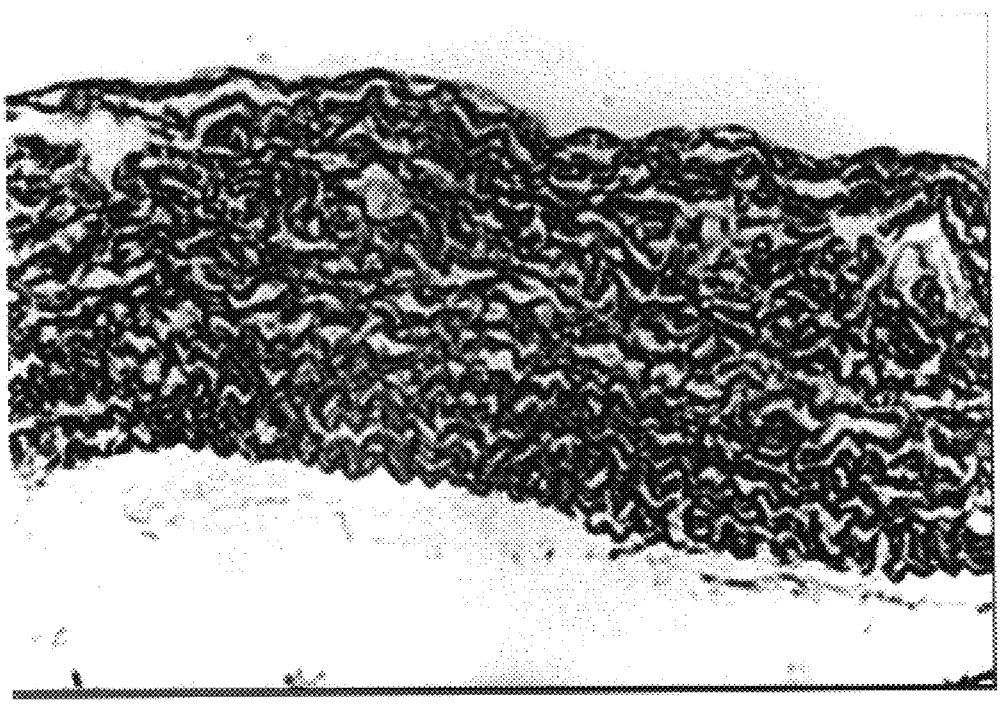
Figure 1D:
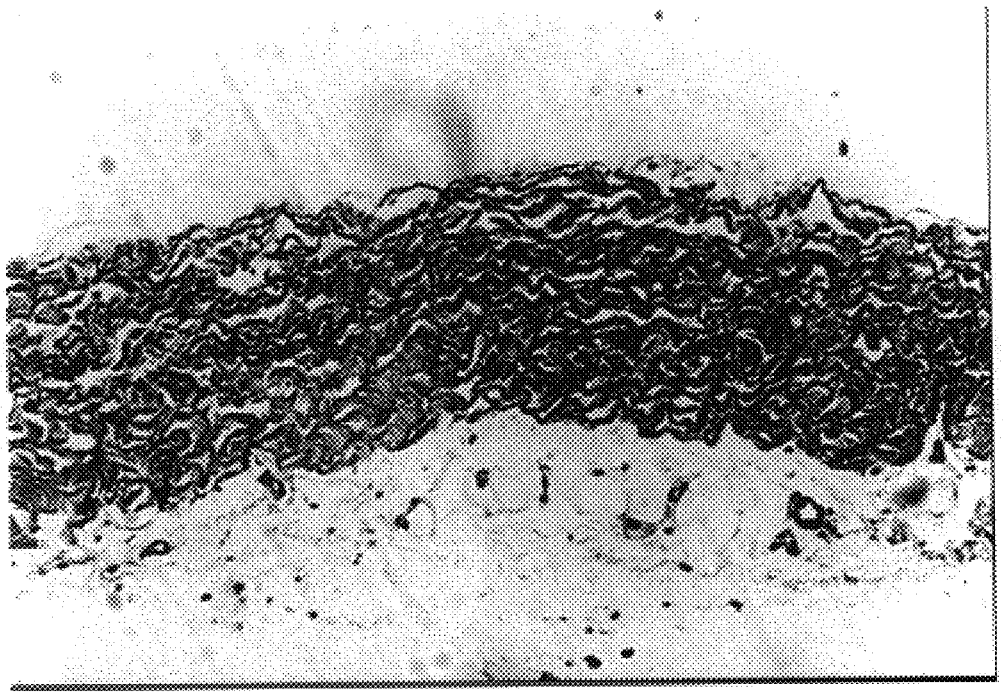
Figure 1E:
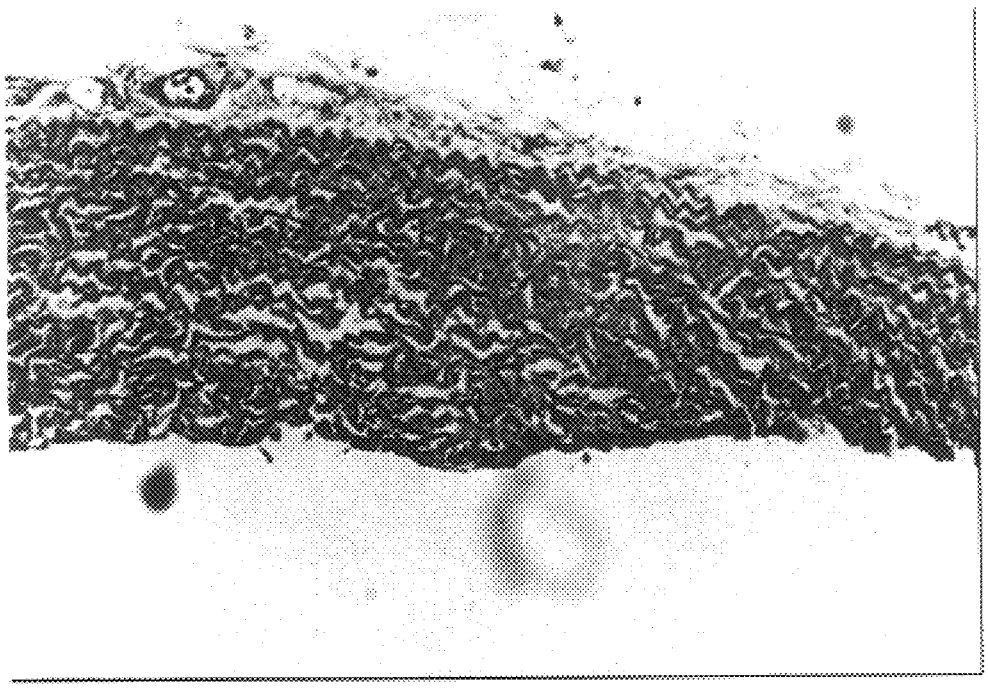
Figure 1F:
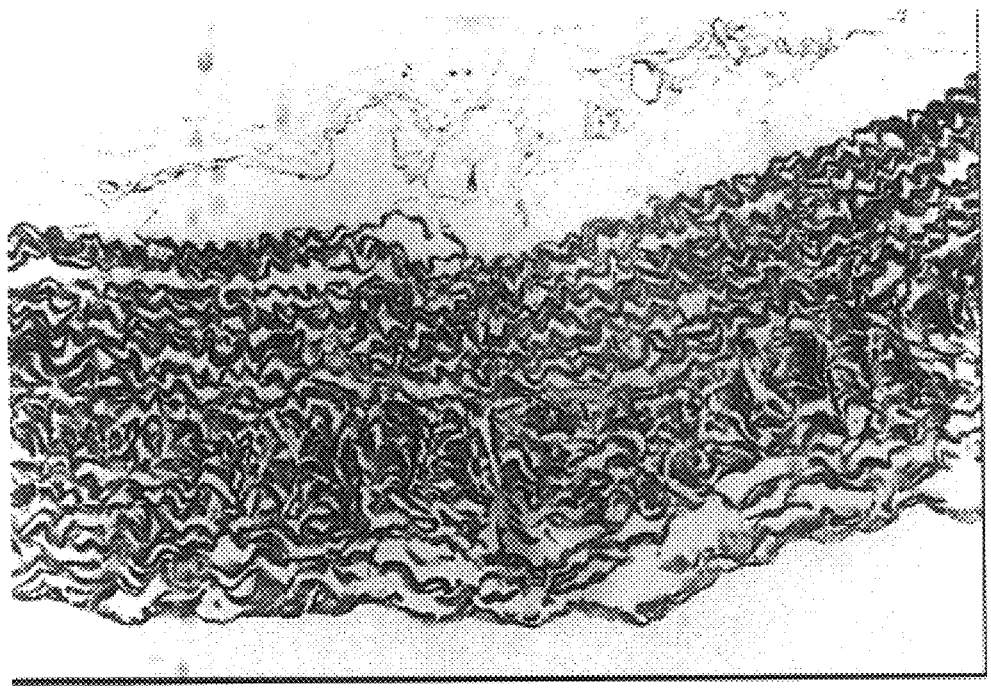
Figure 1G:
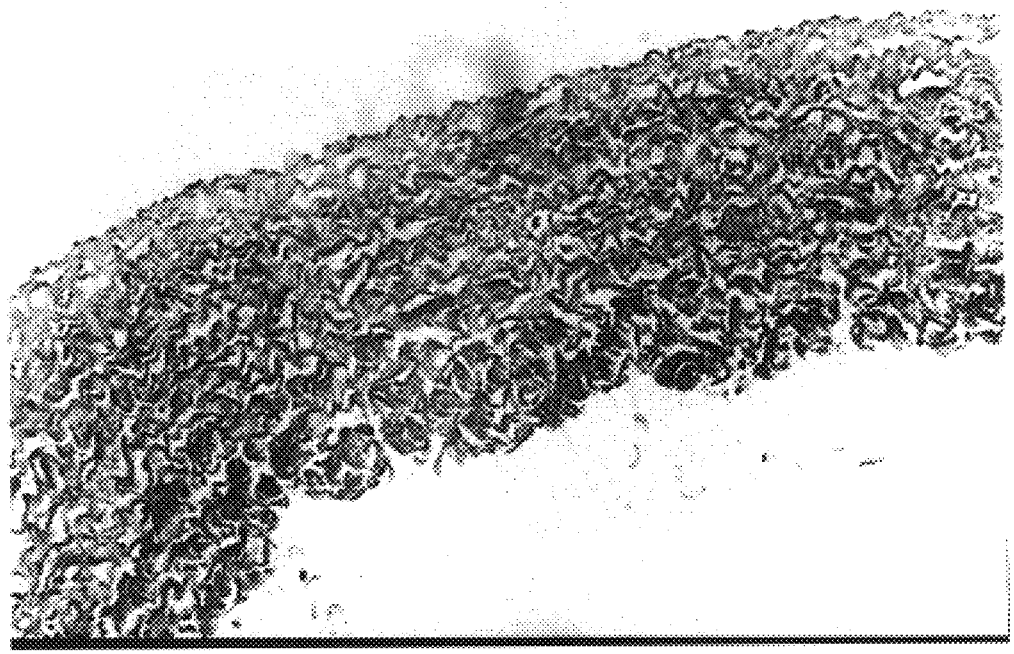
Figure 1H:

FIGS. 1A–H present computer-generated images derived from photomicrographs of the fresh (1A–B), glutaraldehyde-fixed (1C–D), epoxy-fixed (1E–F), and genipin-fixed (1G–H) tissue samples before and after collagenase degradation, respectively. After degradation, the fresh tissue had disintegrated into pieces (FIG. 1B). In contrast, the collagen fibril structures of the glutaraldehyde-fixed and genipin-fixed tissues remained intact after collagenase degradation (FIGS. 1D and 1H), while slight disintegration of the collagen fibrils of the epoxy-fixed tissue was observed (FIG. 1F).

Figure 2:
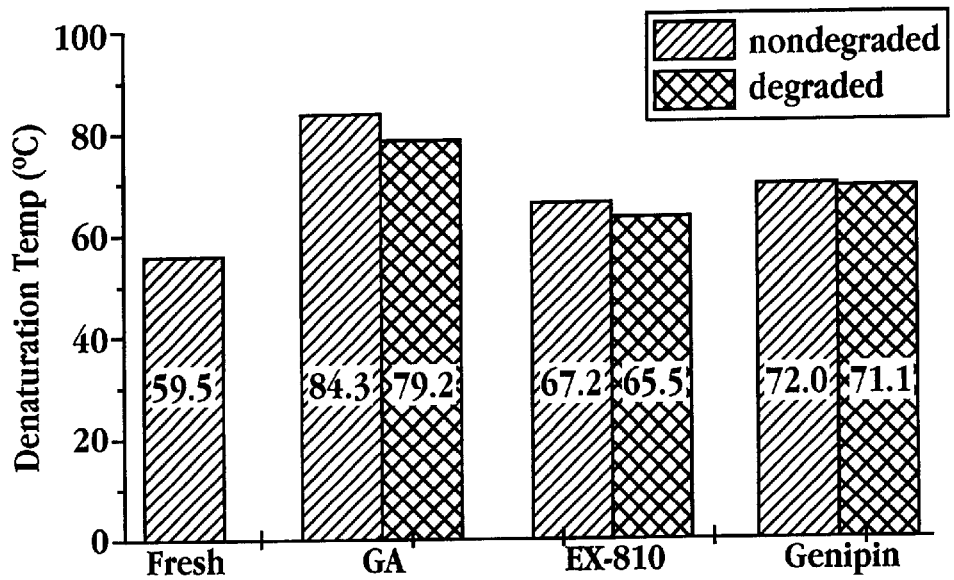
FIGS. 2 and 3 show the denaturation temperatures of the test samples from FIG. 1, obtained before and after collagenase or pronase degradation, respectively.
Figure 3:
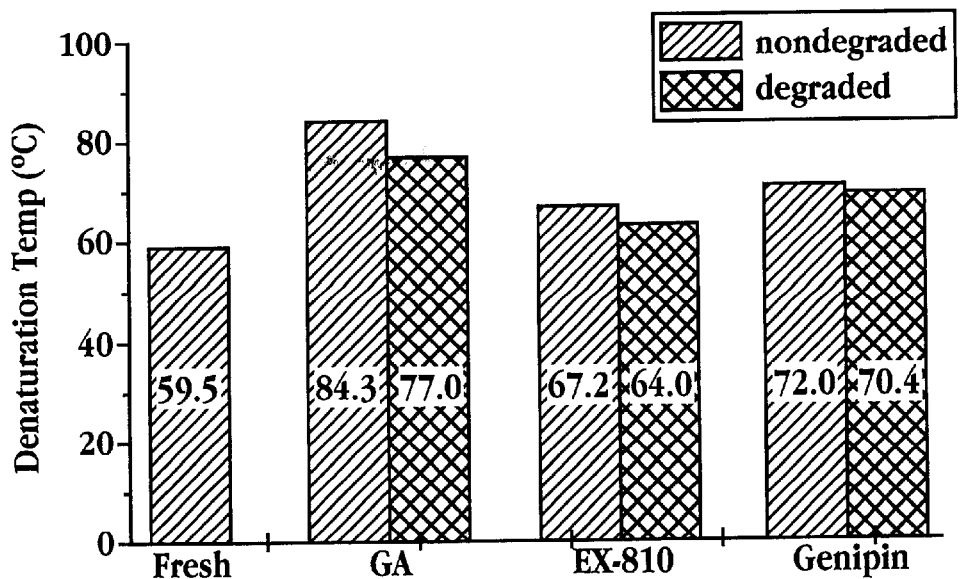

The denaturation temperature of each test sample was measured by a Perkin Elmer differential scanning calorimeter (Model DSC 7, Norwalk, Conn., USA). FIGS. 2 and 3 give the denaturation temperatures of the above-designated test samples before and after collagenase or pronase degradation, respectively. No denaturation temperatures of the fresh (uncrosslinked) tissues could be determined after collagenase or pronase degradation, due to the extensive disintegration of these samples. As illustrated in the figures, the decline in denaturation temperature for the genipin-fixed tissue (<2%) was less than that for the glutaraldehyde- and epoxy-fixed tissues (3–10%).

Figure 4:
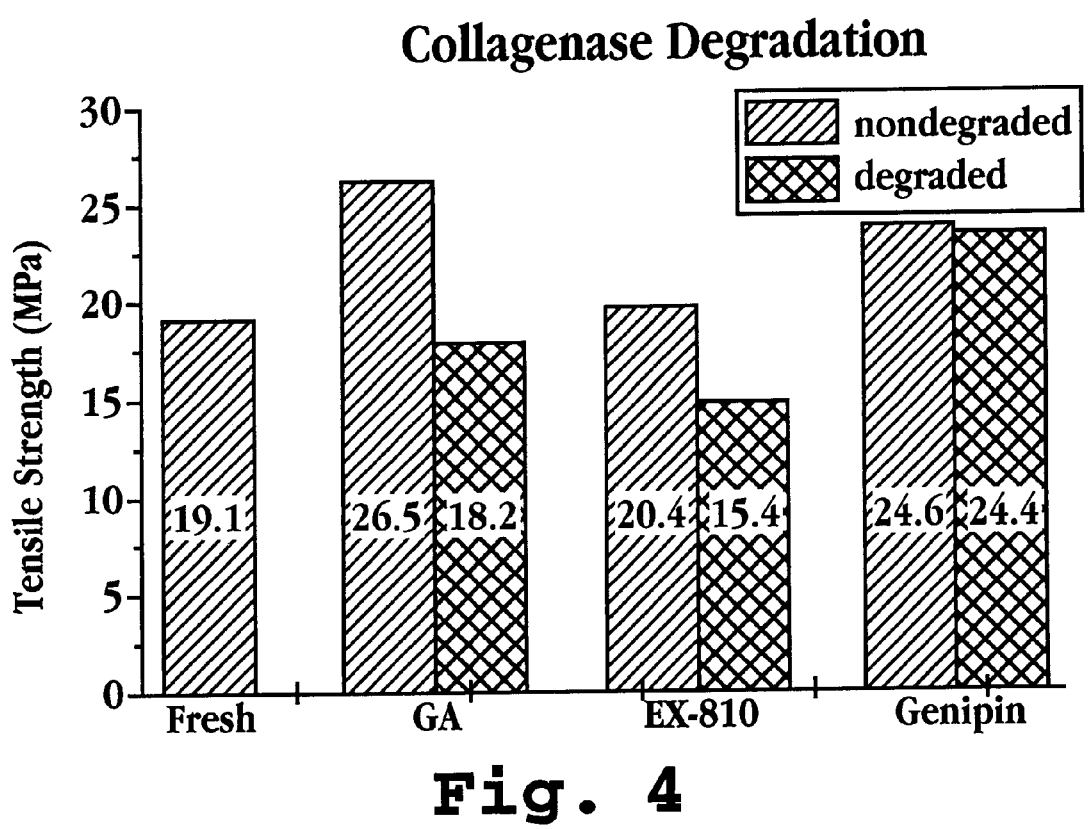
FIG. 4 shows the tensile strengths of fresh, glutaraldehyde-fixed, epoxy-fixed, and genipin-fixed tissues before and after collagenase degradation.

The genipin-fixed tissues also showed superior retention of tensile strength. Tissue strips were cut from each test sample before and after in vitro degradation for tensile strength measurements. Stress-strain curves of the tissue strips were determined by uniaxial measurements using an Instron Universal Testing Machine (Model 4302) at a constant speed of 50 mm/min. FIG. 4 shows the results of the tensile stress measurements of the fresh, glutaraldehyde-fixed, epoxy-fixed, or genipin-fixed tissues before and after collagenase degradation. The tensile stress of the fresh tissue was recorded as zero after degradation, again due to the extensive disintegration of this sample. As shown in the figure, the reduction in tensile stress for the genipin-fixed tissue was minimal (<1%), and was significantly less than for the glutaraldehyde-fixed and epoxy-fixed tissues (31% and 25%, respectively).

The above results show that genipin-fixed collagenous tissues have thermal stability and tensile strengths similar to glutaraldehyde-fixed tissues, and that they retain their tensile strength and thermal stability to a significantly greater degree than the glutaraldehyde- and epoxy-fixed tissues upon treatment with collagen-degrading enzymes.

B. Stability in Subcutaneous Implantation

1. Short Term Study (Four Weeks)

A subcutaneous implantation study was conducted, using a growing rat model, to evaluate the stability (change in denaturation temperature and tensile strength) and level of calcium deposition in implanted pericardial tissues crosslinked with genipin. Fresh (uncrosslinked), glutaraldehyde-fixed, and epoxy-fixed tissues were also tested. The tissue samples were prepared as described in Example 2. A subcutaneous implant study was conducted on 6-week-old male Wistar rats, and implants were retrieved at 1 week and 4 weeks post-implantation.

Fresh samples were generally thinner than the crosslinked samples at 1 week post implantation, and were completely degraded at 4 weeks. At 4 weeks, a thin layer of host tissue was observed on the genipin-fixed samples, but not on the glutaraldehyde- or epoxy-fixed samples. The genipin-fixed samples thus appeared to be the most biocompatible by this standard.

Figure 5:
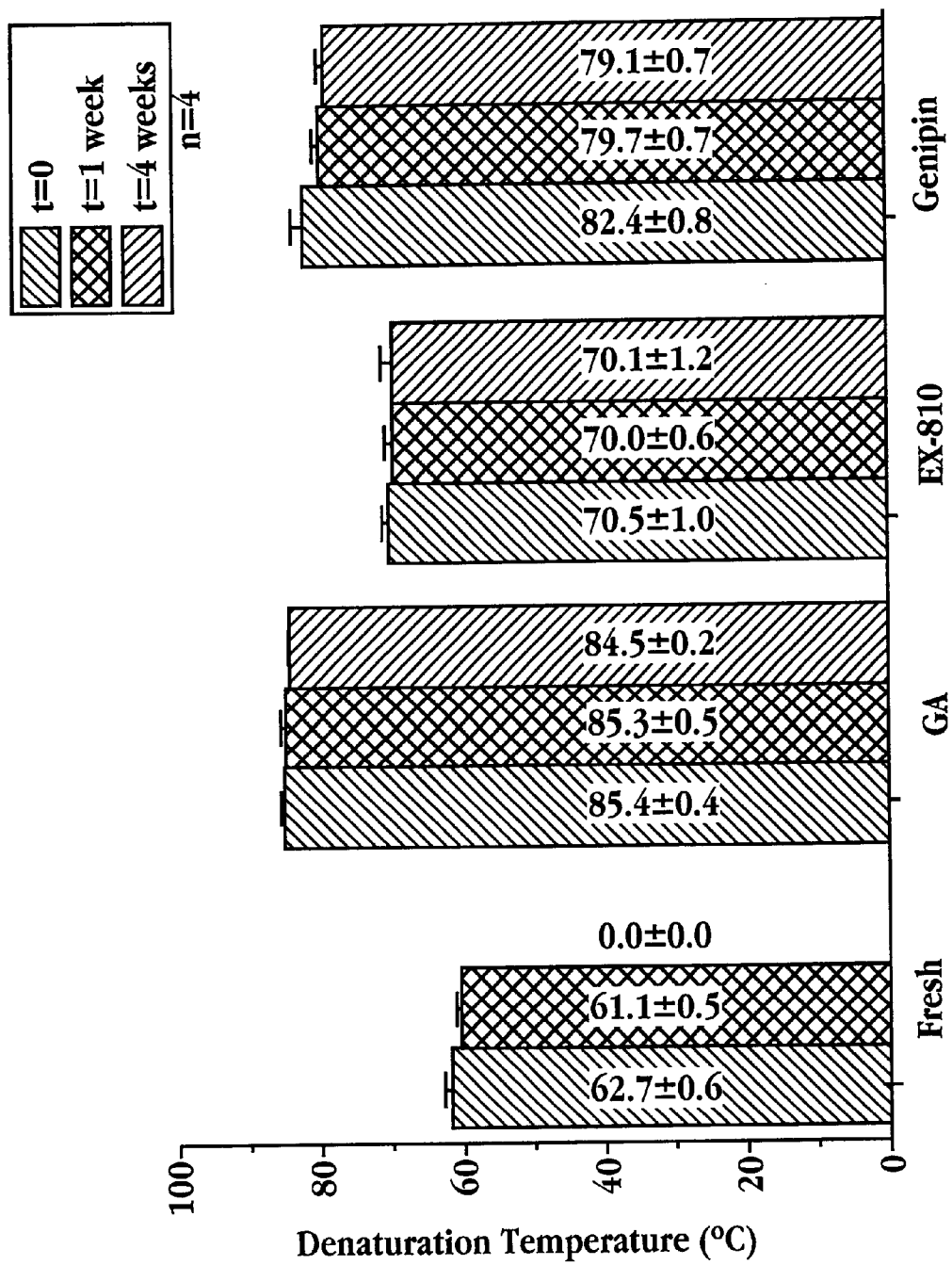
FIG. 5 shows the denaturation temperatures of fresh, glutaraldehyde-fixed (GA), epoxy-fixed (EX-810), and genipin-fixed pericardial tissues before (t=0) and after (t=1 wk; t=4 wks) subcutaneous implantation in a growing rat model.

The denaturation temperatures and tensile strengths of the samples were determined, as described above, before and after implantation. As shown in FIG. 5, the denaturation temperatures of the genipin-fixed and glutaraldehyde-fixed samples were similar and were significantly higher than that of the epoxy-fixed samples. This suggests a higher crosslinking density in the genipin-fixed and glutaraldehyde-fixed tissues. In all cases, little degradation in denaturation temperature was observed up to four weeks post-implantation.

Figure 6:
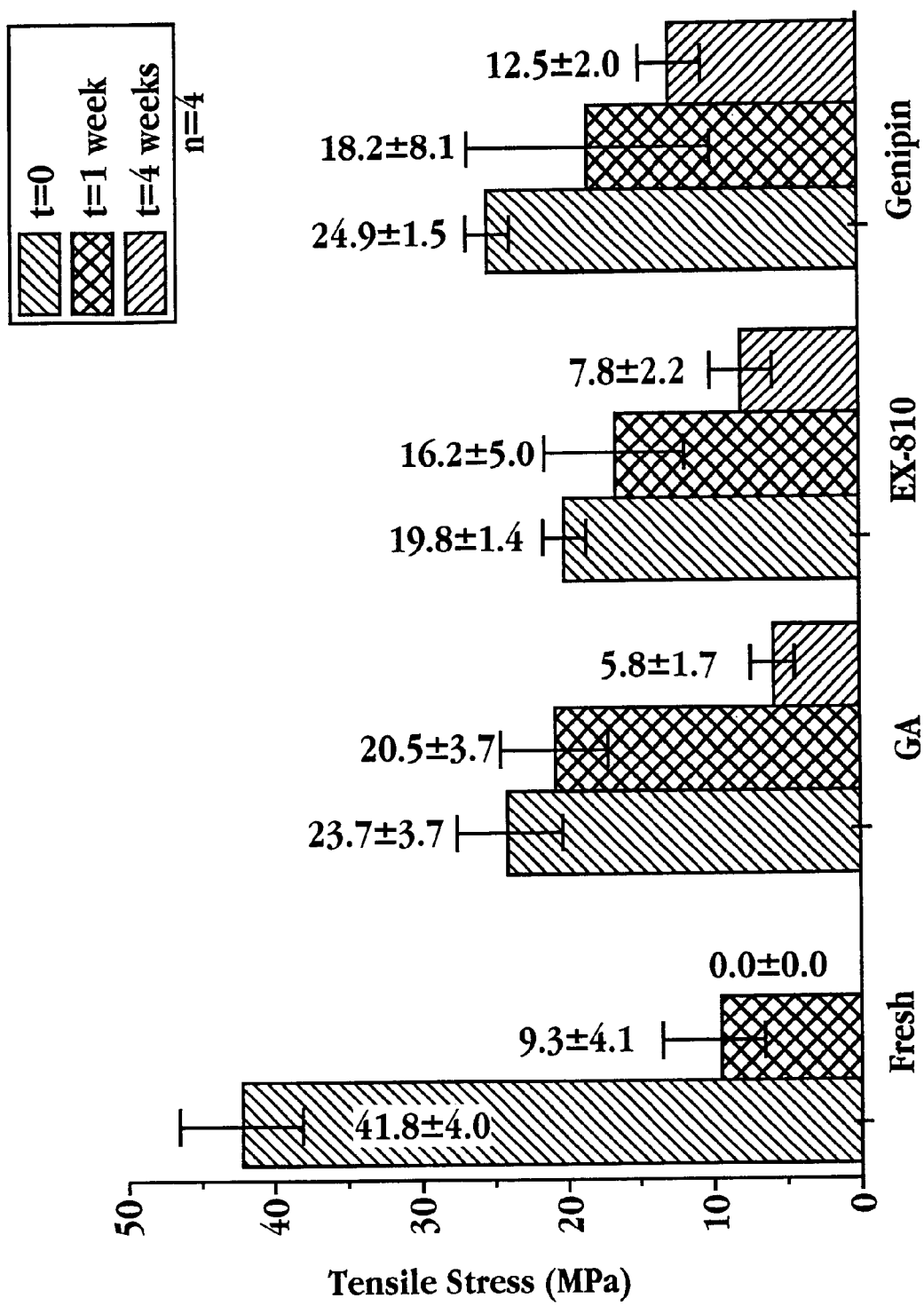
FIG. 6 shows the tensile strengths of the samples from FIG. 5, before and after implantation.

As shown in FIG. 6, the tensile strength of the genipin-fixed sample was superior at all stages to that of the epoxy-fixed sample. Pre-implantation and at 1 week post-implantation, the tensile strengths of the genipin- and glutaraldehyde-fixed samples were similar. At 4-weeks post-implantation, however, the genipin-fixed sample had substantially greater tensile strength than the glutaraldehyde-fixed sample.

Figure 7:
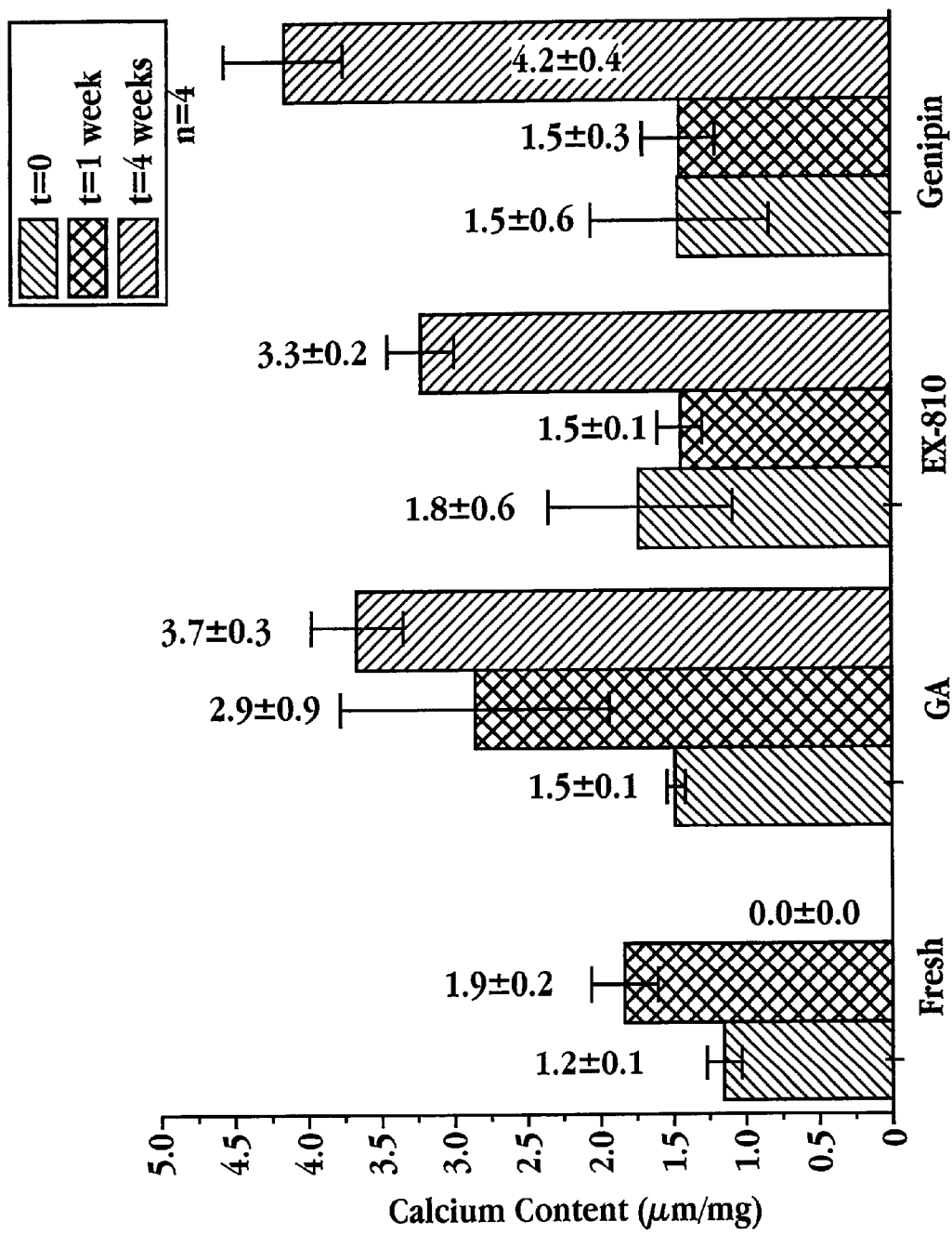
FIG. 7 shows the calcium content of the samples from FIG. 5, before and after implantation.

FIG. 7 shows the amount of calcium deposited during implantation, as determined by atomic absorption spectroscopy as described in Example 3. As the figure shows, calcium deposition was fairly similar for the genipin- and epoxy-fixed samples, and was less, at 1 week, than that shown for the uncrosslinked sample. The glutaraldehyde-fixed sample showed substantially greater calcium deposition at 1 week, and a level similar to the other two fixed samples at 4 weeks.

The above results show that collagenous tissues crosslinked with genipin show similar or superior stability and biocompatibility to those crosslinked with glutaraldehyde, without the attendant toxicity of glutaraldehyde and related compounds.

2. Long Term Study (Twelve Weeks)

Sterilized samples of fresh (uncrosslinked), glutaraldehyde-, epoxy-, and genipin-fixed porcine pericardia were implanted subcutaneously in a growing rat model (6-week-old male Wistar) under aseptic conditions, as described for the short-term study above. Four samples, one from each studied group, were implanted on the upper back of the animal model; the other four samples, again one from each studied group, were implanted on the lower back, in reverse order. Each test sample was approximately 0.5 cm in width and 2 cm in height. The order of the test samples in each row was rotated from animal to animal. The implanted samples were then retrieved at 1 week (n=4), 4 weeks (n=4), and 12 weeks (n=8) postoperatively.

At retrieval, each retrieved sample was examined and photographed. It was noted that the retrieved fresh tissue was significantly thinner than the glutaraldehyde-, epoxy-, and genipin-fixed counterparts. At 4 weeks postoperatively, six out of the eight implanted fresh tissue samples were found to be completely degraded, while the other two fresh samples were being absorbed by the host tissue. In contrast, the glutaraldehyde-, epoxy-, and genipin-fixed tissues remained intact throughout the entire course of the study.

Scanning electron microscopy (SEM) was used to examine the surface morphology of each retrieved sample. The samples used for the SEM examination were first fixed with 2% glutaraldehyde in 0.1M sodium cacodylate (pH 7.4) and then postfixed in 1% osmium tetroxide. Subsequently, the samples were dehydrated in a graded series of ethanol solutions, critical-point dried with carbon dioxide, and spattered with gold film. The examination was performed with a Hitachi Model S-800 scanning electron microscope.

FIGS. 9A and 9E show computer-generated images derived from the SEM micrographs of the fresh tissue before implantation and retrieved at 1 week postoperatively. As shown in FIG. 9E, the fresh tissue retrieved at 1 week postoperatively was already degraded extensively. The glutaraldehyde- and genipin-fixed tissues retrieved at 12 weeks postoperatively (FIGS. 9F and 9H, respectively) were slightly degraded as compared to their counterparts before implantation (FIGS. 9B and 9D, respectively). The degree of degradation for the epoxy-fixed tissue (FIGS. 9G vs. 9C) was more extensive than for its glutaraldehyde- and genipin-fixed counterparts.

The samples used for light microscopy were fixed in 10% phosphate buffered formalin for at least 3 days and prepared for histopathological examination. In the histopathological examination, the fixed samples were embedded in paraffin, sectioned into a thickness of 5 $\mu$m, and stained with hematoxylin and eosin (H&E). The stained sections of each test sample were examined by light microscopy (Nikon Microphoto-FXA) for tissue inflammatory reaction and photographed with 100 ASA Kodachrome film.

Figure 10A:
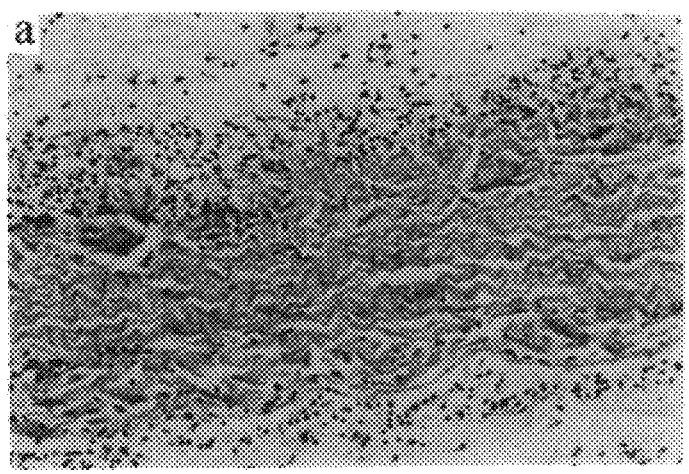
FIGS. 10A–C are computer-generated images derived from photomicrographs (magnification×200) of (A) glutaraldehyde-fixed tissue, (B) epoxy-fixed tissue, and (C) genipin-fixed tissue retrieved 12 weeks after implantation and stained with hematoxylin and eosin.
Figure 10B:
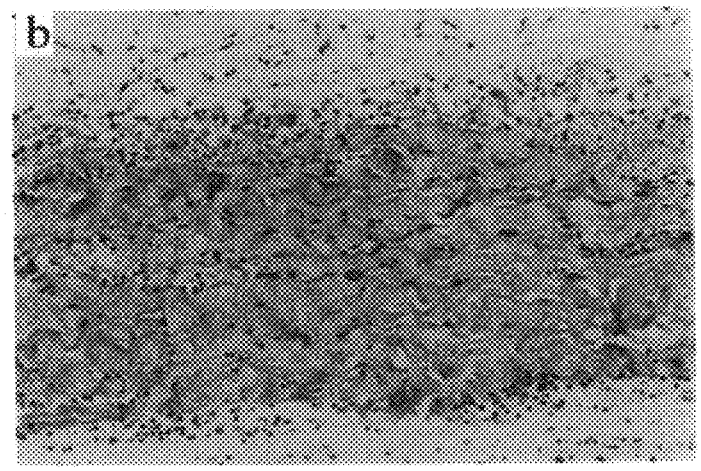
Figure 10C:
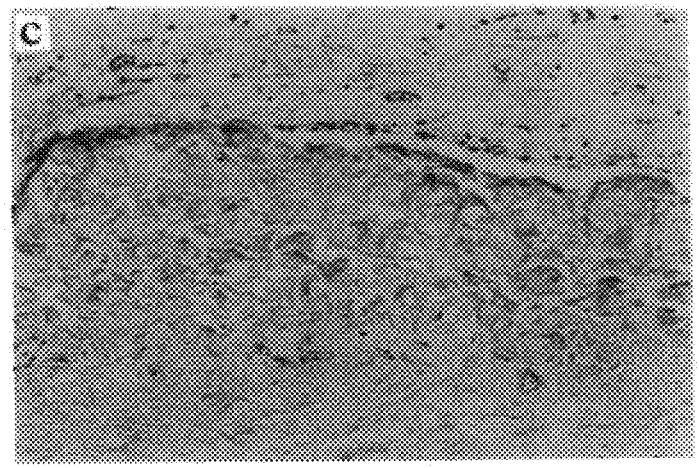

Computer-generated images derived from the photomicrographs of the glutaraldehyde-, epoxy-, and genipin-fixed tissues retrieved at 12-week postoperatively are shown in FIGS. 10(A–C). It should be noted that no photomicrograph of the fresh tissue retrieved at this time could be made, due to its complete degradation. The inflammatory reaction of the genipin-fixed tissue was significantly less than that of its glutaraldehyde- and epoxy-fixed counterparts, indicating superior biocompatibility of the genipin-fixed tissue, due to its significantly lower toxicity (see Section C, below).

Atomic absorption analysis was used to determine the calcium content of each retrieved sample, as described in Example 3. Calcium content data for the fresh, glutaraldehyde-, epoxy-, and genipin-fixed tissues before implantation and those retrieved at 1-, 4-, and 12-weeks postoperatively are presented in Table 1, expressed as $\mu$g calcium per mg of dry tissue weight. It should be noted that no data could be obtained for the fresh (uncrosslinked) tissues retrieved at 4- and 12 weeks postoperatively, due to their complete disintegration. As shown in the table, no significant differences in calcium content were observed in this study between the samples before implantation and those retrieved at various implantation times.

TABLE 1

Calcium Content ($\mu$g Calcium/mg Dry Tissue Weight) Before Implantation and at Different Implantation Times

| Implantation Duration | Fresh | Glut | Epoxy | Genipin |
|---|---|---|---|---|
| 0 wk (n = 4) | 1.2 ± 0.1 | 1.5 ± 0.1 | 1.8 ± 0.6 | 1.5 ± 0.6 |
| 1 wk (n = 4) | 1.9 ± 0.2 | 2.9 ± 0.9 | 1.5 ± 0.1 | 1.5 ± 0.3 |
| 4 wks (n = 4) | N/A* | 1.8 ± 0.3 | 1.6 ± 0.2 | 2.1 ± 0.4 |
| 12 wks (n = 8) | N/A | 1.6 ± 0.5 | 1.9 ± 0.9 | 1.7 ± 0.6 |

Data are presented in mean ± standard deviation.
N/A*: Data were not available due to complete degradation of the tissue.

C. Cytotoxicity Study

The cells used in this study were human foreskin fibroblasts derived from the foreskin of a normal newborn infant. The cells were cultured in 3.5-cm diameter petri dishes ($10^5$ cells per dish) in Dulbecco's modified eagle medium (DMEM, Gibco 430-2800EG, Grand Island, N.Y., USA) supplemented with 10% fetal calf serum (Hyclone Laboratories, Logan. Utah, USA). The cell culture was maintained in a humidified incubator at 37° C. with 10% $CO_2$ in air for 24 h.

The medium was then replaced with genipin (Challenge Bioproducts Co., Taichung, Taiwan) in DMEM, at a concentration of 0 (blank), 10, 100, or 1,000 ppm ($\mu$g/ml). Glutaraldehyde and an epoxy compound (ethylene glycol diglycidyl ether, Denacol® EX-810, Nagase Chemicals, Ltd., Osaka, Japan) were also tested, at a concentration of 1, 5, or 10 ppm.

After 24 h of culture, the cells were washed twice with phosphate buffered saline, and the medium was replaced with a fresh DMEM medium without any test crosslinking reagent. Finally, the cells were incubated for another two weeks. During this period, the medium was changed once.

Figure 8A:
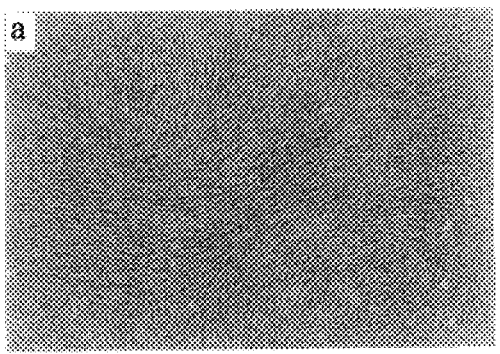
FIGS. 8A–8D are computer-generated images derived from photomicrographs (magnification ×100) of cells cultured in (A) control medium and in medium supplemented with (B) 1 ppm glutaraldehyde, (C) 5 ppm epoxy compound, and (D) 1,000 ppm genipin.
Figure 8B:
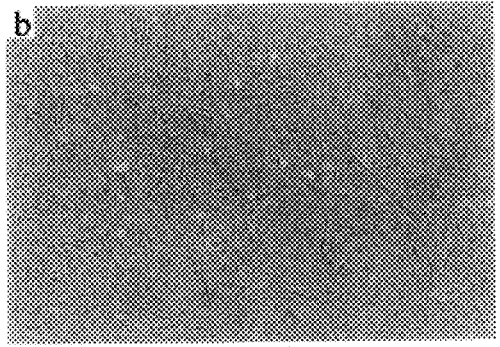
Figure 8C:
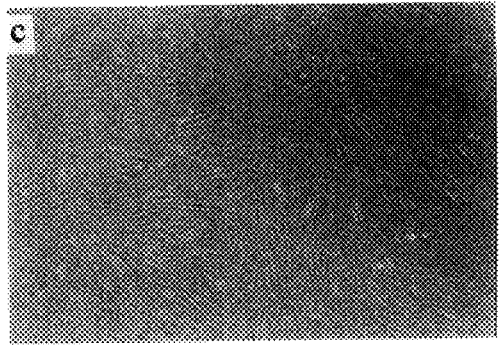
Figure 8D:
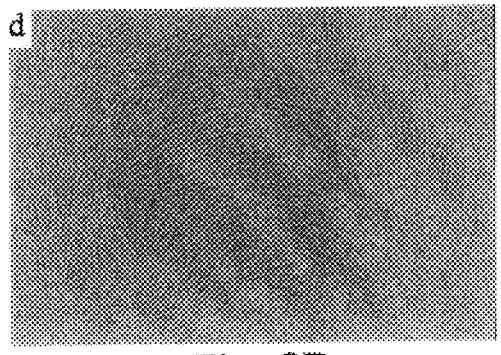

FIG. 8A shows a computer-generated image derived from a photomicrograph of a control culture of human fibroblasts, cultured as described above, but without any test crosslinking reagent. As shown in the figure, the cells observed in the petri dish were confluent. FIGS. 8B–8D show computer-generated images derived from photomicrographs of the human fibroblasts cultured in media supplemented with different crosslinking reagents at the following concentrations: 1 ppm glutaraldehyde (8B), 5 ppm epoxy (8C), and 1000 ppm genipin (8A).

The cell density was lowest in the medium supplemented with glutaraldehyde (FIG. 8B) and slightly higher in the epoxy-treated culture. Both were much less than that found in the control medium. In contrast, the cell density seen in the medium supplemented with genipin (FIG. 8D) was significantly greater than those supplemented with glutaraldehyde or epoxy compound, in spite of a much higher concentration of genipin used. This result suggests that the cytotoxicity of genipin is significantly lower than that of glutaraldehyde and the epoxy compound.

IV. Crosslinking of Hemoglobin

Hemoglobin polymerized with genipin has a stable tetramer structure, and the molecular weight distribution remains unchanged over an extended storage period, as shown by the results described in this Section.

In crosslinking of hemoglobin for use as a blood substitute, it is desirable to obtain a distribution of hemoglobin oligomers consisting of 2–9 units, while minimizing the formation of overpolymerized hemoglobin (>9 units and >500 KDa) and methemoglobin. In support of the present invention, studies were carried out on the effect of several factors on product distribution obtained from treatment of hemoglobin with genipin. These factors, discussed individually below, are (a) reaction time, (b) concentration of hemoglobin, (c) molar ratio of genipin/hemoglobin, (d) reaction temperature, (e) buffer pH and (f) addition of lysine as a quenching reagent.

For each reaction, hemoglobin was initially purged with CO gas in order to decrease methemoglobin formation during reaction. Product distribution was analyzed by HPLC as described in Example 3, below.

A. Reaction Time

Product distribution was observed over 2–48 hr, where hemoglobin concentration was 14 g/dl and genipin concentration was 15 mM, at pH 7.0 and 4° C. At 12 hr, the level of $Hb_1$ (unpolymerized hemoglobin) was reduced to 60.15%, and methemoglobin had increased only from 14.98% to 18.81%, as shown in Table 2. At more than 15 hr, over-polymerized hemoglobin (>500 KDa) was observed, the desired crosslinked hemoglobin had increased minimally, and methemoglobin increased rapidly. The optimal reaction time under these conditions was therefore about 12–15 hr.

TABLE 2

MOLECULAR WEIGHT DISTRIBUTION AND METHEMOGLOBIN FORMATION AT DIFFERENT REACTION TIMES

| Reaction Time | $Hb_1$ % | $Hb_2$ % | $Hb_{3-4}$ % | $Hb_{5-9}$ % | $Hb_{>9}$ % | Met Hb % |
|---|---|---|---|---|---|---|
| 2 hr | 91.69 | 6.31 | | | | 14.98 |
| 6 hr | 76.22 | 12.84 | 7.51 | | | 15.31 |
| 9 hr | 65.44 | 15.98 | 15.24 | 2.00 | | 17.66 |
| 12 hr | 60.51 | 17.32 | 15.80 | 6.95 | | 18.81 |
| 15 hr | 45.98 | 18.00 | 16.97 | 13.73 | 5.32 | 22.83 |
| 24 hr | 40.95 | 17.99 | 17.34 | 16.87 | 9.02 | 24.56 |
| 48 hr | 39.87 | 18.89 | 15.43 | 14.92 | 12.89 | 30.33 |

*$Hb_n$: number of crosslinked hemoglobin units
*Met Hb: Methemoglobin
*Initial percent methemoglobin was 15.69%.

B. Hemoglobin Concentration

Genipin concentration, pH, and reaction temperature were the same as used for Section A, above. A hemoglobin concentration in the range of 10–14 g/dl was found to be appropriate for the polymerization reaction. When the concentration is less than 10 g/dl, the desired crosslinked hemoglobin (<500 KDa) increases with increasing concentration of hemoglobin, but the reaction rate is slow. For concentrations higher than 14 g/dl, both overpolymerized hemoglobin and methemoglobin are increased, as shown in Table 3.

TABLE 3

MOLECULAR WEIGHT DISTRIBUTION AND METHEMOGLOBIN FORMATION AT DIFFERENT HEMOGLOBIN CONCENTRATIONS

| Hemoglobin Concentration | $Hb_1$ % | $Hb_2$ % | $Hb_{3-4}$ % | $Hb_{5-9}$ % | $Hb_{>9}$ % | Met Hb % |
|---|---|---|---|---|---|---|
| 7 g/dl | 77.15 | 10.69 | 10.12 | 2.04 | | 11.21 |
| 10 g/dl | 70.89 | 13.23 | 12.69 | 3.19 | | 12.69 |
| 12 g/dl | 66.10 | 15.98 | 15.24 | 2.68 | | 13.58 |
| 14 g/dl | 59.15 | 18.59 | 16.42 | 5.84 | | 13.10 |
| 16 g/dl | 44.39 | 16.27 | 18.14 | 16.56 | 3.33 | 17.88 |

*$Hb_n$: number of crosslinked hemoglobin units
*Met Hb: Methemoglobin
*Initial percentage of methemoglobin was equal to 10.08

C. Genipin/Hemoglobin Ratio

No changes were made to hemoglobin concentration (14 g/dl), temperature or pH. The optimum molar ratio of genipin/hemoglobin was found to be in the range of 6/1 to 9/1. At molar ratios less than 6/1, the reaction rate was very slow and the yield of polymerized hemoglobin was low. Molar ratios greater than 9/1 did not increase the desired polymerized hemoglobin, but did produce higher levels of methemoglobin and overpolymerized hemoglobin, as shown in Table 4.

TABLE 4

MOLECULAR WEIGHT DISTRIBUTION AND METHEMOGLOBIN FORMATION AT DIFFERENT GENIPIN/HEMOGLOBIN MOLAR RATIOS

| Genipin/Hb Molar Ratio | $Hb_1$ % | $Hb_2$ % | $Hb_{3-4}$ % | $Hb_{5-9}$ % | $Hb_{>9}$ % | Met Hb % |
|---|---|---|---|---|---|---|
| 6/1 | 67.66 | 15.79 | 12.63 | 3.92 | | 19.38 |
| 7/1 | 64.55 | 16.59 | 13.42 | 5.44 | | 19.77 |
| 8/1 | 63.15 | 17.10 | 13.80 | 5.95 | | 20.01 |
| 9/1 | 62.45 | 18.03 | 15.05 | 7.11 | | 22.44 |
| 10/1 | 47.58 | 17.44 | 16.98 | 12.83 | 5.17 | 25.59 |

*Hb: hemoglobin
*$Hb_n$: number of crosslinked hemoglobin units
*Met Hb: Methemoglobin
*Initial percent methemoglobin was 22.18%.

D. Buffer DH

For this series of reactions, temperature was 4° C., reaction time was 15 hours, and concentrations of hemoglobin and genipin were 10 g/dl and 15 mM (molar ratio 7/1). Aqueous solutions of potassium hydrogen phosphate (0.05 M, pH 4.0), sodium phosphate (0.001 M, pH 9.0), sodium borate (0.01 M, pH 9.0), and sodium carbonate/sodium bicarbonate (0.19 M/0.18 M) were used to prepare buffers having pH values of 5.5, 7.5 and 9.5, respectively. As shown in Table 5, neutral and basic pH were most favorable for the polymerization of hemoglobin.

TABLE 5

MOLECULAR WEIGHT DISTRIBUTION AND METHEMOGLOBIN FORMATION AT DIFFERENT PH VALUES

| pH Value | $Hb_1$ % | $Hb_2$ % | $Hb_{3-4}$ % | $Hb_{5-9}$ % | $Hb_{>9}$ % | Met Hb % |
|---|---|---|---|---|---|---|
| 5.5 | 72.07 | 14.22 | 11.47 | 2.24 | | 15.66 |
| 7.5 | 70.89 | 14.42 | 11.66 | 3.03 | | 16.10 |
| 9.5 | 49.61 | 17.49 | 16.45 | 12.01 | | 13.89 |

*$Hb_n$: number of crosslinked hemoglobin units
*Met Hb: Methemoglobin
*Initial percent methemoglobin was 17.12%.

E. Reaction Temperature

The concentrations of hemoglobin and genipin were unchanged for this series of reactions, and the pH was adjusted to 7.0. A range of temperatures from 4° C. to 40° C. was employed, giving the results shown in Table 6. As shown, higher temperatures induce a higher degree of polymerization of hemoglobin. At 30–40° C., 60–65% of unpolymerized hemoglobin reacts within 2 hr. Not surprisingly, however, higher temperatures also increased formation of overpolymerized hemoglobin and methemoglobin as well as bacteria production. Suitable temperatures were between 4° C. and 20° C.

TABLE 6

MOLECULAR WEIGHT DISTRIBUTION AND METHEMOGLOBIN FORMATION AT DIFFERENT REACTION TEMPERATURES

| Reaction Temp. | $Hb_1$ % | $Hb_2$ % | $Hb_{3-4}$ % | $Hb_{5-9}$ % | $Hb_{>9}$ % | Met Hb % |
|---|---|---|---|---|---|---|
| 4° C. | 94.18 | 5.82 | | | | 14.99 |
| 10° C. | 89.30 | 8.05 | 2.65 | | | 15.33 |
| 20° C. | 71.72 | 15.54 | 12.31 | 0.43 | | 15.98 |
| 30° C. | 38.00 | 15.20 | 16.74 | 21.35 | 8.71 | 17.99 |
| 40° C. | 34.38 | 13.65 | 15.49 | 20.21 | 16.27 | 19.15 |

*$Hb_n$: number of crosslinked hemoglobin units
*Met Hb: Methemoglobin
*Initial percent methemoglobin was 10.08%.

F. Addition of Lysine as Terminator

Lysine is commonly used as a terminator for protein crosslinking reactions. Two polymerizations were carried out simultaneously, and to one was added lysine at 14.5 hr. Concentration of hemoglobin and genipin was 14 g/dl and 15 mM, as above, reaction time was 15 hr, and reaction temperature was maintained at 4° C. As shown in Table 7, lysine was effective in quenching polymerization and reducing the level of overpolymerized hemoglobin.

TABLE 7

EFFECT OF LYSINE QUENCHING AGENT ON MOLECULAR WEIGHT DISTRIBUTION AND METHEMOGLOBIN FORMATION IN HEMOGLOBIN POLYMERIZATION

| Quencher | $Hb_1$ % | $Hb_2$ % | $Hb_{3-4}$ % | $Hb_{5-9}$ % | $Hb_{>9}$ % | Met Hb % |
|---|---|---|---|---|---|---|
| Blank | 45.98 | 18.00 | 16.97 | 13.73 | 5.32 | 15.69 |
| Lysine | 45.97 | 18.81 | 18.97 | 15.93 | 0.32 | 14.58 |

*$Hb_n$: number of crosslinked hemoglobin units
*Met Hb: Methemoglobin
*Initial percent methemoglobin was 12.08%.

EXAMPLES

The following examples illustrate but in no way are intended to limit the present invention.

Example 1

Stability of Crosslinked Collagenous Tissues to Degradative Enzymes

Fresh porcine pericardia procured from a slaughterhouse were used as raw materials. The tissue samples were immediately transferred into cold saline after removal and shipped for fixation. Five percent genipin solution buffered with phosphate buffered saline (pH 7.4) was used to crosslink the biological tissue. The treatment was conducted at 37° C. for 3 days. After fixation, the biological tissue was rinsed in deionized water for 60 minutes. Subsequently, the fixed tissue was sterilized with a 70% ethanol solution for 7 days at 37° C. Glutaraldehyde- and epoxy-fixed counterparts were used as controls. A 0.625% solution of glutaraldehyde was used for fixation. The epoxy reagent was a 4% solution of ethylene glycol diglycidyl ether, Denacol®EX-810, obtained from Nagase Chemicals, Ltd., Osaka, Japan.

Light microscopy was used to examine the changes in collagen fibril structure of each test sample before and after collagenase or pronase degradation. The test samples were fixed in a 10% formalin solution and prepared for histological examination. In the histological examination, sections of each test sample, before and after degradation, were stained with hematoxylin and eosin.

The denaturation temperature of each test sample was measured by a Perkin Elmer differential scanning calorimeter (Model DSC 7, Norwalk, Conn., USA). Results are described above and shown in FIGS. 2 and 3. Tissue strips were cut from each test sample before and after in vitro degradation for tensile strength measurements. Stress-strain curves of the tissue strips were determined by uniaxial measurements using an Instron Universal Testing Machine (Model 4302) at a constant speed of 50 m/min. Results are described above and shown in FIG. 4.

Example 2

Subcutaneous Implantation Study

Fresh porcine pericardia, as described above, were used as raw materials. Samples were rinsed and trimmed to remove blood and fat before fixing with genipin (5% solution), epoxide (4% solution of Denacol® EX-810, Nagase Chemicals, Ltd., Osaka, Japan) or glutaraldehyde (0.625% solution) for 3 days at 37° C. The amount of solution used in each case was about 200 ml for a 6×6 cm porcine pericardium. The epoxy solution was buffered with 0.21M sodium carbonate/0.02M sodium bicarbonate (pH 10.5), while the glutaraldehyde and genipin solutions were buffered with 0.01 M phosphate buffered saline (pH 7.4, Sigma Chemical Co., St. Louis, Mo.). The fixed pericardia were sterilized with a series of ethanol solutions having increasing concentration (20%–75%) for approximately 5 hours, and finally rinsed several times in sterilized phosphate buffered saline.

A subcutaneous implant study was conducted on 6-week-old male Wistar rats under aseptic conditions. Implants were retrieved at 1 and 4 weeks post-implantation. The denaturation temperatures and tensile strengths were determined as in Example 1, and the calcium level was determined by atomic absorption spectroscopy. Results are described above and shown in FIGS. 5–7.

Example 3

Determination of Calcium Content of Implanted Tissue Samples

The retrieved tissues samples were lyophilized for 24 h and weighed. The lyophilized sample was then immersed in a 6 N HCl solution (approx. 3 mg lyophilized tissue/3 mL 6N HCl) and subsequently hydrolyzed in a microwave hydrolysis system (MDS-2000, CEM Co., Matthews, N.C., USA) for 45 min. Finally, the hydrolyzed sample was diluted with a solution of 5% lanthanum chloride in 3N HCl solution. The calcium content of each test sample was determined by an atomic absorption spectrophotometer (Model AA-100, Perkin Elmer Inc., Norwalk, Conn., USA).

Example 4

Polymerization of Hemoglobin

Figure 11:
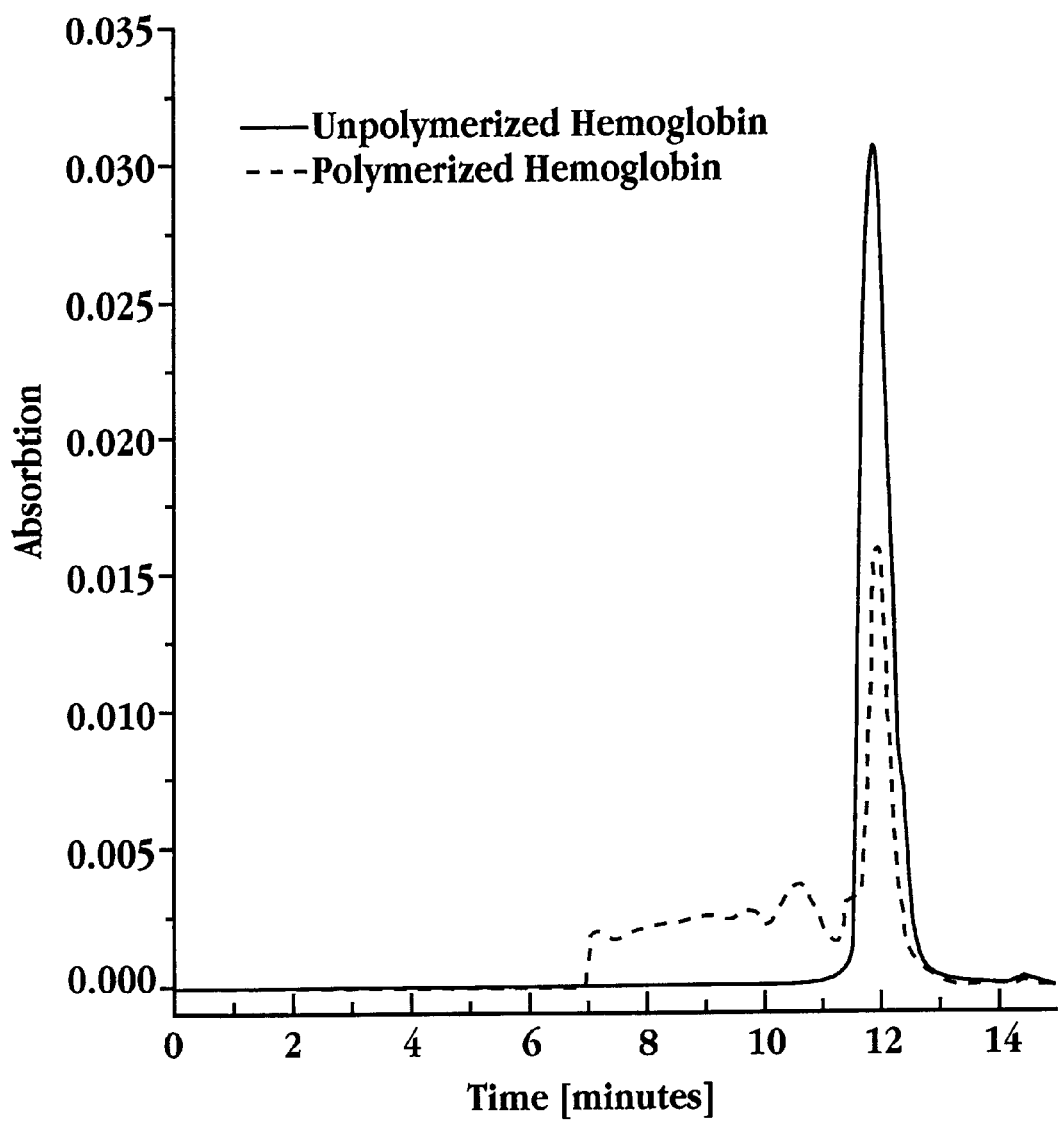
FIG. 11 shows a chromatographic trace obtained from HPLC of polymerized and unpolymerized hemoglobin.

Hemoglobin solution was purged with carbon monoxide for 1 hour at 4° C., then genipin was added to the solution. Reaction time, concentrations, temperature and pH were varied as described above. Molecular weight distribution (degree of crosslinking) and percentage of methemoglobin were analyzed using high performance chromatography on a TSK 3000 SW gel filtration column (mobile phase solvent 0.1M phosphate buffer, 0.3 M NaCl, pH=7; flow rate 0.8 ml/min; detector at 410 nm and 280 nm). A typical profile is shown in FIG. 11.

What is claimed is:

1. A method of providing a biocompatible implant, comprising (i) procuring a tissue material comprising genipin-crosslinkable collagenous tissue, wherein the tissue material is characterized by suitable tensile strength, and (ii) crosslinking said tissue material with genipin to produce a crosslinked structure, said crosslinked structure having stability to degradative enzymes, low acute toxicity, and durability as the biocompatible implant.

2. The method of claim 1, wherein said genipin-crosslinkable collagenous tissue comprises an amine containing molecule.

3. The method of claim 1, wherein said tissue material comprises gelatin, the gelatin being derived from a collagen source.

4. The method of claim 1, wherein said crosslinked structure comprises a prosthetic heart valve.

5. The method of claim 1, wherein said crosslinked structure comprises a ligament replacement.

6. The method of claim 1, wherein said crosslinked structure comprises a vascular graft.

7. A method of preparing a biocompatible adhesive comprising crosslinking a gelatin with an amount of genipin effective to yield a desired adhesiveness and consistency, wherein said gelatin is derived from hydrolytic treatment of collagen or a collagen-containing tissue.

8. A composition suitable for use in a blood substitute, comprising hemoglobin crosslinked with genipin.

9. The composition of claim 8, wherein the crosslinked hemoglobin has a mean degree of polymerization greater than 1 and less than about 9.

10. A method of preparing crosslinked hemoglobin, comprising treating hemoglobin with an amount of genipin effective to crosslink said hemoglobin.

11. The method of claim 10, wherein the hemoglobin is treated with an amount of genipin effective to give a mean degree of polymerization greater than 1 and less than about 9.

12. The method of claim 10, wherein said hemoglobin is contacted with said genipin in an aqueous medium having a neutral or basic pH, in a molar ratio of about 6:1 to 9:1, for a period of about 12–15 hours at a temperature of about 4° C. to 20° C.

13. The crosslinked hemoglobin as prepared by the method of claim 12.

14. The method of claim 1, wherein said crosslinked structure comprises a pericardial patch.

15. A method of providing a biocompatible wound dressing comprising: (i) procuring a tissue material comprising genipin-crosslinkable collagenous tissue; (ii) crosslinking said tissue material with genipin to produce a crosslinked structure, said crosslinked structure having stability to degradative enzymes and low acute toxicity as the biocompatible wound dressing; and (iii) fabricating said crosslinked structure to a proper shape and size configured for use as the biocompatible wound dressing.

16. The method of claim 15, wherein said genipin-crosslinkable collagenous tissue comprises an amine containing molecule.

17. The method of claim 15, wherein said tissue material comprises chitosan.

\* \* \* \* \*